United States Patent
Karl et al.

[11] Patent Number: 6,096,912
[45] Date of Patent: *Aug. 1, 2000

[54] SOLUBLE CATALYST SYSTEMS FOR THE PREPARATION OF POLYALK-1-ENES HAVING HIGH MOLECULAR WEIGHTS

[75] Inventors: Eberhard Karl; Werner Roell, both of Constance; Hans Brintzinger, Leimbach-Guntershausen; Bernhard Rieger, Nehren; Udo Stehling, Constance, all of Germany

[73] Assignee: BASF Aktiengesellschaft, Ludwigshafen, Germany

[ * ] Notice: Under 35 U.S.C. 154(b), the term of this patent shall be extended for 381 days.

[21] Appl. No.: 08/642,491

[22] Filed: May 3, 1996

Related U.S. Application Data

[62] Division of application No. 08/375,278, Jan. 19, 1995, Pat. No. 5,514,760, which is a continuation of application No. 08/158,777, Dec. 1, 1993, abandoned, which is a division of application No. 07/900,427, Jun. 18, 1992, Pat. No. 5,296,434.

Foreign Application Priority Data

Jun. 18, 1991 [DE] Germany .............................. 41 20 009

[51] Int. Cl.[7] .................................................. C07F 17/00
[52] U.S. Cl. ................ 556/11; 556/12; 556/22; 556/23; 556/43; 556/53; 526/127; 526/160; 526/351; 526/943; 502/103; 502/117; 502/155; 502/158
[58] Field of Search ................... 556/11, 12, 22, 556/23, 43, 53; 526/127, 160, 351, 943; 502/103, 117, 155, 158

[56] References Cited

U.S. PATENT DOCUMENTS 4,794,096  12/1988  Ewen ........................................ 502/117

FOREIGN PATENT DOCUMENTS

| | | |
|---|---|---|
| 0 185 918 A2 | 7/1986 | European Pat. Off. . |
| 0 283 739 A2 | 9/1988 | European Pat. Off. . |
| 0 284 708 A1 | 10/1988 | European Pat. Off. . |
| 0 316 155 B1 | 5/1989 | European Pat. Off. . |
| 0 355 447 A2 | 2/1990 | European Pat. Off. . |
| 2 207 136 | 1/1989 | United Kingdom . |

*Primary Examiner*—Porfirio Nazario-Gonzalez
*Attorney, Agent, or Firm*—Keil & Weinkauf

[57] ABSTRACT

Abstract of the Disclosure: Catalyst systems for the polymerization of $C_2$–$C_{10}$-alk-1-enes contain, as active components, a) a metallocene complex of the general formula I

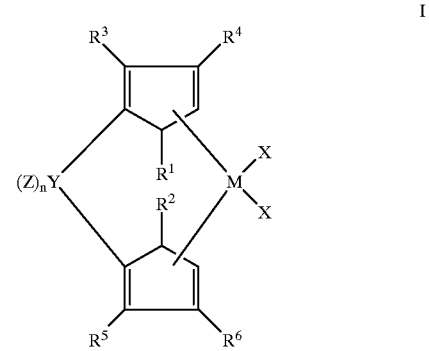

where M is titanium, zirconium, hafnium, vanadium, niobium or tantalum, X is halogen or $C_1$–$C_8$-alkyl, Y is carbon, phosphorus, sulfur, silicon or germanium, Z is $C_1$–$C_8$-alkyl, $C_3$–$C_{10}$-cycloalkyl or $C_6$–$C_{10}$-aryl, $R^1$ and $R^2$ are identical or different and are each $C_1$–$C_4$-alkyl, $R^3$ to $R^6$ are identical or different and are each hydrogen or $C_1$–$C_8$-alkyl, or two adjacent radicals $R^3$ and $R^4$ and $R^5$ and $R^6$ in each case together form a hydrocarbon ring system of 4 to 15 carbon atoms and n is 0, 1 or 2, and b) an open-chain or cyclic alumoxane compound of the general formula II or III

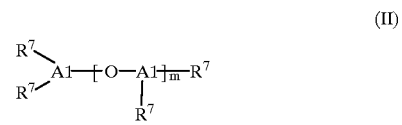

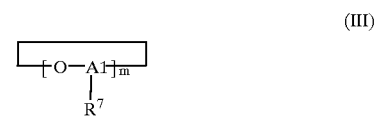

where $R^7$ is $C_1$–$C_4$-alkyl and n is from 5 to 30.

The novel catalyst systems are particularly suitable for the preparation of polyalk-1-enes having high molecular weights.

7 Claims, No Drawings

SOLUBLE CATALYST SYSTEMS FOR THE PREPARATION OF POLYALK-1-ENES HAVING HIGH MOLECULAR WEIGHTS

This is a division of application Ser. No. 08/375,278, filed Jan. 19, 1995, now U.S. Pat. No. 5,514,760, which is a FWC of Ser. No. 08/158,777, filed on Dec. 1, 1993, now abandoned, which is a division of Ser. No. 07/900,427, filed Jun. 18, 1992 now U.S. Pat. No. 5,296,434.

The present invention relates to catalyst systems for the polymerization of $C_2$–$C_{10}$-alk-1-enes, containing, as active components, a) a metallocene complex of the general formula I

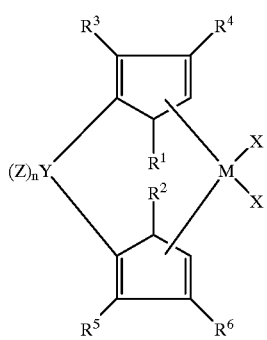

where M is titanium, zirconium, hafnium, vanadium, niobium or tantalum, X is halogen or $C_1$–$C_8$-alkyl, Y is carbon, phosphorus, sulfur, silicon or germanium, Z is $C_1$–$C_8$-alkyl, $C_3$–$C_{10}$-cycloalkyl or $C_8$–$C_{10}$-aryl, $R^1$ and $R^2$ are identical or different and are each $C_1$–$C_4$-alkyl, $R^3$ to $R^6$ are identical or different and are each hydrogen or $C_1$–$C_8$-alkyl, or two adjacent radicals $R^3$ and $R^4$ and $R^5$ and $R^6$ in each case together form a hydrocarbon ring system of 4 to 15 carbon atoms and n is 0, 1 or 2, and b) an open-chain or cyclic alumoxane compound of the general formula II or III

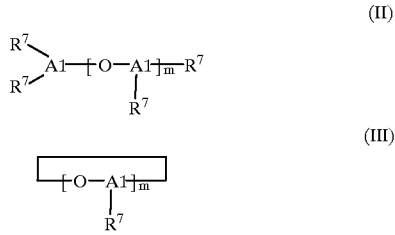

where $R^7$ is $C_1$–$C_4$-alkyl and n is from 5 to 30.

The present invention furthermore relates to a process for the preparation of polymers of propylene with the aid of these catalyst systems and to the polymers obtainable by this process.

In addition to the insoluble Ziegler-Natta catalysts, soluble catalysts systems can also be used for the polymerization of alk-1-enes. Said soluble catalyst systems are complex compounds of metals of subgroups IV and V of the Periodic Table with organic ligands, which are used in conjunction with oligomeric aluminum compounds (EP-A 185 918, EP-A 283 739 and GB-A 2 207 136). The complex compounds used in these catalyst systems contain, as organic ligands, generally cyclopentadienyl groups which form π bonds with the transition metal. Transition metal complexes which, in addition to organic ligands, also contain halogens bonded to the metal atom are also frequently used as catalysts.

EP-A 284 708 and 316 155 and EP-A 355 447 describe soluble catalyst systems for the polymerization of alk-1-enes, in which bis(cyclopentadienyl) complexes of metals of subgroup IV of the Periodic Table are used as complex compounds, the two cyclopentadienyl rings being bonded by an alkyl-substituted silicon, tin or germanium atom or by sulfur atoms. Transition metal complexes in which the cyclopentadienyl rings are substituted by alkyl and which contain, as further ligands, two halogens bonded to the transition metal may also be used. The oligomeric aluminum compounds preferably used are linear or cyclic alumoxane compounds of the general formula II or III.

With the aid of such catalyst systems it is possible to obtain polymers of propylene which have, inter alia, a relatively narrow molecular weight distribution. In contrast to polypropylene which is prepared by using insoluble Ziegler-Natta catalysts, the molecular weights of the polypropylenes obtained in this manner are substantially lower, so that they cannot be used for many applications where polymers having molecular weights of more than 100,000 are employed.

A possible method for increasing the molecular weights of polyolefins is to reduce the reaction temperature during the polymerization. Propylene polymers having molecular weights of about 50,000 ($\overline{M}_w$) are obtainable in this manner, for example in EP-A 355 447. In this measure, however, the increase in the molecular weights is associated with a substantial decrease in the polymerization rate, ie. a substantial increase in the reaction time, so that the reduction of the reaction temperature has an adverse effect on the cost-efficiency of the production process.

It is an object of the present invention to overcome this disadvantage and to provide an improved soluble catalyst system which makes it possible to prepare polyalk-1-enes with high molecular weights in a very economical manner.

We have found that this object is achieved by the soluble catalyst systems defined at the outset.

According to the invention, metal complexes of the general formula I, where titanium, zirconium, hafnium, vanadium, niobium or tantalum are used as the central atom M, are used. In the metal complexes to be used according to the invention and of the general formula I, the central atom is bonded on the one hand via π bonds to substituted cyclopentadienyl groups and on the other hand to further substituents X, which may be fluorine, chlorine, bromine or iodine or $C_1$–$C_8$-alkyl. Metallocene complexes of the general formula I in which M is zirconium or hafnium and X is chlorine or bromine are preferably used.

Furthermore, the metal complex to be used according to the invention and of the general formula I contains, in addition to the central atom and its substituents and the substituted cyclopentadienyl groups, also a bridge member $(Z)_nY$, which bonds the two cyclopentadienyl groups to one another. Here, Y is carbon, phosphorus, sulfur, silicon or germanium, Z is $C_1$–$C_8$-alkyl, $C_3$–$C_{10}$-cycloalkyl or $C_1$–$C_{10}$-aryl and n is 0, 1 or 2.

In the preferably used metallocene complexes of the general formula I, Y is carbon, sulfur or silicon, Z is $C_1$–$C_4$-alkyl and n is 2.

A further important component of the metal complexes to be used according to the invention and of the general formula I are substituted cyclopentadienyl groups. These each contain radicals $R^1$ or $R^2$ which are identical or different and are each $C_1$–$C_4$-alkyl, in particular methyl, ethyl, isopropyl or tert-butyl. These cyclopentadienyl groups also have the substituents $R^3$ to $R^6$, where $R^3$ to $R^6$ are identical or different and are each hydrogen or $C_1$–$C_8$-alkyl, or two adjacent radicals $R^3$ and $R^4$ and $R^5$ and $R^6$ in each case together form a hydrocarbon ring system of 4 to 15 carbon atoms. Metallocene complexes of the general formula I whose cyclopentadienyl groups have substituents $R^3$ to $R^6$ where $R^3$ and $R^5$ are each $C_1$–$C_4$-alkyl and $R^4$ and $R^6$ are each hydrogen and two adjacent radicals $R^3$ and $R^4$ and $R^5$ and $R^6$ in each case together form a hydrocarbon ring system of 4 to 12 carbon atoms, for example an indenyl system, are preferably used. The number of carbon atoms of the hydrocarbon ring systems includes the two carbon atoms of the cyclopentadienyl system which serve as linkage points with the substituents $R^3$ to $R^6$ so that, for example when $R^3$ and $R^4$ and $R^5$ and $R^6$ are in each case cyclohexyl, there are altogether two hydrocarbon ring systems, each of 6 carbon atoms.

Examples of particularly preferred metallocene complexes include dimethylsilanediylbis-(2-methylindenyl)-zirconium dichloride, diethylsilanediylbis-(2-methylindenyl)-zirconium dichloride, dimethylsilanediylbis-(2-methylindenyl)-zirconium dichloride, dimethylsilanediylbis-(2-isopropylindenyl)-zirconium dichloride, dimethylsilanediylbis-(2-tert-butylindenyl)-zirconium dichloride, diethylsilanediylbis-(2-methylindenyl)-zirconium dibromide, dimethylthiobis-(2-methylindenyl)-zirconium dichloride, dimethylsilanediylbis-(2-methyl-5-methylcyclopentadienyl)-zirconium dichloride, dimethylsilanediylbis-(2-methyl-5-ethylcyclopentadienyl)-zirconium dichloride, dimethylsilanediylbis-(2-ethyl-5-isopropylcyclopentadienyl)-zirconium dichloride, dimethylsilanediylbis-(2-methylindanyl)-zirconium dichloride, dimethylsilanediylbis-(2-methylbenzindenyl)-zirconium dichloride and dimethylsilanediylbis-(2-methylindenyl)-hafnium dichloride.

The synthesis of such complexes can be carried out by conventional methods, the reaction of the correspondingly substituted cycloalkenyl anions with halides of titanium, zirconium, hafnium, vanadium, niobium or tantalum being preferred. Examples of corresponding preparation processes are described in, inter alia, Journal of Organometallic Chemistry 369 (1989), 359–370.

In addition to the metallocene complex, the novel catalyst system also contains linear or cyclic alumoxane compounds of the general formula II or III

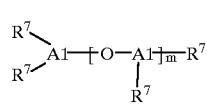

(II)

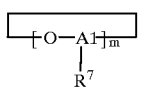

(III)

where $R^7$ is preferably methyl or ethyl and m is preferably from 10 to 25.

The preparation of these alumoxane compounds is usually carried out by reacting a solution of trialkyl-aluminum with water and is described in, inter alia, EP-A 284 708 and U.S. Pat. No. 4,794,096.

As a rule, the alumoxanes obtained are a form of mixtures of both linear and cyclic chain molecules of different lengths, so that m should be regarded as an average value. The alumoxane compound may also contain trialkylaluminum compounds whose alkyl groups are each of 1 to 8 carbon atoms, for example trimethyl-, triethyl- or methyldiethylaluminum.

In the polymerization of alk-1-enes with the aid of the novel catalyst system, it is advantageous to use the metallocene complex a) and the alumoxane compound b) in amounts such that the atomic ratio of aluminum from the alumoxane b) to the transition metal from the metal-locene complex a) is from 10:1 to $10^6$:1, in particular from 10:1 to $10^4$:1. The two catalyst components can be introduced into the polymerization reactor individually in any order or as a mixture. A particularly reactive soluble catalyst system is obtainable when the metallocene complex a) and the alumoxane compound b) are mixed with one another from 5 to 60, preferably from 10 to 40, minutes before the actual polymerization. The catalyst activated in this manner can then be used immediately.

With the aid of these soluble catalyst systems, it is possible to prepare polymers of alk-1-enes. These are understood as meaning homo- and copolymers of $C_2$–$C_{10}$-alk-1-enes, ethylene, propylene, but-1-ene, pent-1-ene and hex-1-ene preferably being used as monomers. The novel catalyst systems are particularly suitable for the preparation of polypropylene and of copolymers of propylene with minor amounts of other $C_2$–$C_{10}$-alk-1-enes, in particular of ethylene and but-1-ene.

The preparation of these polymers can be carried out in the conventional reactors used for the polymerization of alk-1-enes, either batchwise or, preferably, continuously. Suitable reactors include continuously operated stirred kettles and a number of stirred kettles connected in series may also be used.

The polymerization is carried out at from 0.1 to 3,000, preferably from 0.5 to 2,500, bar and from −20 to 300° C., preferably from +10 to +150° C. The polymerization time is usually from 0.5 to 10 hours.

Polymerization reactions carried out with the aid of the novel catalyst system can be effected in the gas phase, in liquid monomers or in inert solvents. The polymerization in solvents, in particular in liquid hydrocarbons, such as benzene or toluene, is preferably used. In this case, it is advantageous if from $10^{-4}$ to $10^{-1}$ mol of aluminum as alumoxane is used per liter of the solvent.

The average molecular weight of the polymers formed can be controlled by the methods conventionally used in polymerization technology, for example by the addition of regulators, such as hydrogen, or by changing the reaction temperatures.

Polymers prepared with the aid of the novel catalyst systems have a high molecular weight and a narrow molecular weight distribution. They can also be prepared at relatively high temperatures, with the result that the polymerization time can be limited. Owing to these properties, the polymers obtainable using the novel catalyst systems are particularly suitable for the production of films and moldings.

EXAMPLES FOR THE PREPARATION OF POLYPROPYLENE

Example 1

350 ml of dry toluene were initially taken in a stirred autoclave having a useful volume of 1 l, and a solution of 0.45 g of methylalumoxane (average chain length m=20) in 30 ml of toluene was then added. $7.6 \cdot 10^{-3}$ mol of aluminum was used per liter of the solvent. A solution of 15 mg of dimethylsilanediylbis-(2-methylindenyl)-zirconium dichloride (corresponding to $31.2 \cdot 10^{-6}$ mol) in 15 ml of toluene was then added, so that the atomic ratio of aluminum to zirconium was 244:1. This mixture was first stirred for 30 minutes at 50° C., after which propylene was forced in under a pressure of 2 bar and polymerization was carried out for 4 hours and 40 minutes. The polymerization was effected at 50° C. and 2 bar. Thereafter, unconsumed propylene was removed and a mixture of 1 l of methanol and 10 ml of concentrated hydrochloric acid were added to the reaction solution. The precipitated polymer was filtered off, washed with methanol and dried under reduced pressure. 45 g of polypropylene having a weight average molecular weight ($\overline{M}_w$) of 114,200, a number average molecular weight ($\overline{M}_n$) of 41,500 and a molecular weight distribution ($\overline{M}_w/\overline{M}_n$) of 2.75 were obtained.

Example 2

The procedure was similar to that of Example 1, 350 ml of dry toluene likewise being initially taken and a solution of 0.45 g of methylalumoxane (m=20) in 30 ml of toluene then being added. Thereafter, a suspension of 0.5 mg of dimethylsilanediylbis-[3,3'-(2-methylbenz-indenyl)]-zirconium dichloride in 20 ml of toluene was added, so that the atomic ratio of aluminum to zirconium was 8950:1. The further procedure was then as described under Example 1.

51.4 g of polypropylene having a weight average molecular weight ($\overline{M}_w$) of 142,896, a number average molecular weight ($\overline{M}_n$) of 91,917 and a molecular weight distribution of 1.55 were obtained.

Pentad content, measured by $^{13}$C-NMR: amount mmmm= 93.5%.

We claim:

1. A metallocene complex of the formula I

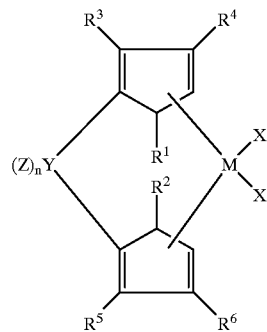

where M is titanium, zirconium, hafnium, vanadium, niobium or tantalum, X is halogen or $C_1$–$C_8$-alkyl, Y is carbon, phosphorus, sulfur, silicon or germanium, Z is $C_1$–$C_8$-alkyl, $C_3$–$C_{10}$-cycloalkyl or $C_6$–$C_{10}$-aryl, $R^1$ and $R^2$ are identical or different and are each $C_1$–$C_4$-alkyl, two adjacent radicals $R^3$ and $R^4$ and $R^5$ and $R^6$ in each case together form, a hydrocarbon ring system of 10 to 15 carbon atoms and n is 0, 1 or 2.

2. A metallocene complex as claimed in claim 1, in which M is hafnium or zirconium.

3. A metallocene complex as claimed in claim 1, in which X is chlorine or bromine.

4. A metallocene complex as claimed in claim 1, in which Y is carbon, sulfur or silicon.

5. A metallocene complex as claimed in claim 1, wherein $R^1$ and $R^2$ are identical or different and are each methyl, ethyl, isopropyl or tert-butyl.

6. A metallocene complex as claimed in claim 1, in which two adjacent radicals $R^3$ and $R^4$ and $R^5$ and $R^6$ in each case together form a hydrocarbon ring system of 10 to 12 carbon atoms.

7. Dimethylsilanediylbis-(2-methylbenzindenyl)-zirconium dichloride.

* * * * *